US00PP37491P2

(12) United States Plant Patent
van Lier

(10) Patent No.: US PP37,491 P2
(45) Date of Patent: Jun. 23, 2026

(54) ***SCABIOSA* PLANT NAMED 'LIER 01'**

(50) Latin Name: *Scabiosa columbaria*
Varietal Denomination: Lier 01

(71) Applicant: Wilhelmus Petrus Johannes Maria van Lier, Meijel (NL)

(72) Inventor: Wilhelmus Petrus Johannes Maria van Lier, Meijel (NL)

(73) Assignee: VAN VLIET NEW PLANTS B.V., Stroe (NL)

( * ) Notice: Subject to any disclaimer, the term of this patent is extended or adjusted under 35 U.S.C. 154(b) by 0 days.

(21) Appl. No.: 19/372,605

(22) Filed: Oct. 29, 2025

(30) Foreign Application Priority Data

Dec. 20, 2024 (QZ) ..... PBR 20243208

(51) Int. Cl.
*A01H 5/02* (2018.01)
*A01H 6/00* (2018.01)

(52) U.S. Cl.
USPC ..... Plt./478

(58) Field of Classification Search
USPC ..... Plt./478
See application file for complete search history.

(56) References Cited

U.S. PATENT DOCUMENTS

PP35,889 P2 * 6/2024 Kim ..... Plt./478

* cited by examiner

*Primary Examiner* — Susan McCormick Ewoldt
*Assistant Examiner* — Zachariah Allan Kay
(74) *Attorney, Agent, or Firm* — Penny J. Aguirre

(57) ABSTRACT

A new cultivar of *Scabiosa* plant named 'Lier 01' that is characterized by its compact plant habit, its floriferous blooming habit, its dark blue flowers, and its moderate growth habit.

2 Drawing Sheets

Botanical classification: *Scabiosa columbaria.*
Variety denomination: 'Lier 01'.

CROSS-REFERENCE TO A RELATED APPLICATION

This application claims priority to European Community Plant Variety Office (CPVO) Plant Breeder's Rights Application No. 2024/3208 filed on Dec. 20, 2024, under 35 U.S.C. 119(f), the entire contents of which is incorporated by reference herein.

BACKGROUND OF THE INVENTION

The present invention relates to a new and distinct cultivar of *Scabiosa columbaria* botanically known as *Scabiosa* 'Lier 01' and will be referred to hereinafter by its cultivar name, 'Lier 01'. The new cultivar of *Scabiosa* is an herbaceous perennial grown for use as a landscape plant.

The new cultivar was discovered by the Inventor in September of 2019 as a naturally occurring branch mutation of *Scabiosa* 'Butterfly Blue' (not patented) that was growing in a container in an active greenhouse in Meijel, the Netherlands.

Asexual propagation of the new cultivar was first accomplished by the Inventor by stem cuttings in September of 2019 in Meijel, The Netherlands. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of 'Lier 01'. These characteristics in combination distinguish 'Lier 01' as a new and distinct cultivar of *Scabiosa.*

1. 'Lier 01' exhibits compact plant habit.
2. 'Lier 01' exhibits a floriferous blooming habit.
3. 'Lier 01' exhibits dark blue flowers.
4. 'Lier 01' exhibits a moderate growth habit.

Butterfly Blue differs form 'Lier 01' in having a less compact plant habit, lighter blue flowers, and a less floriferous blooming habit. 'Lier 01' can be most closely compared to the *Scabiosa* cultivars 'Pincushion Blue' (not patented) and 'Mariposa Blue' (not patented). Both 'Pincushion Blue' and 'Mariposa Blue' are similar to 'Lier 01' in having blue colored flowers. 'Pincushion Blue' differs from 'Lier 01' in having a less compact plant habit and leaflets that are narrower, and in blooming later in the season. 'Mariposa Blue' differs from 'Lier 01' in having a less compact plant habit, more flowers per inflorescence, and a less floriferous blooming habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Van Vliet New Plants, Floral Daily, Plantarium Groen Direkt, HoticultureWeek, Flora Viva, Gabot, Nova, Kientzier, griffin Greenhouse Supplies, Albert Garden, and My News Week.

BRIEF DESCRIPTION OF THE DRAWINGS

The accompanying color photographs illustrate the overall appearance and distinct characteristics of a 6-month-old plant of the new *Scabiosa* as grown outdoors in a 17-cm container in Boskoop, The Netherlands.

The photograph in FIG. 1 provides a side view of 'Lier 01' in bloom.

Figure 1:
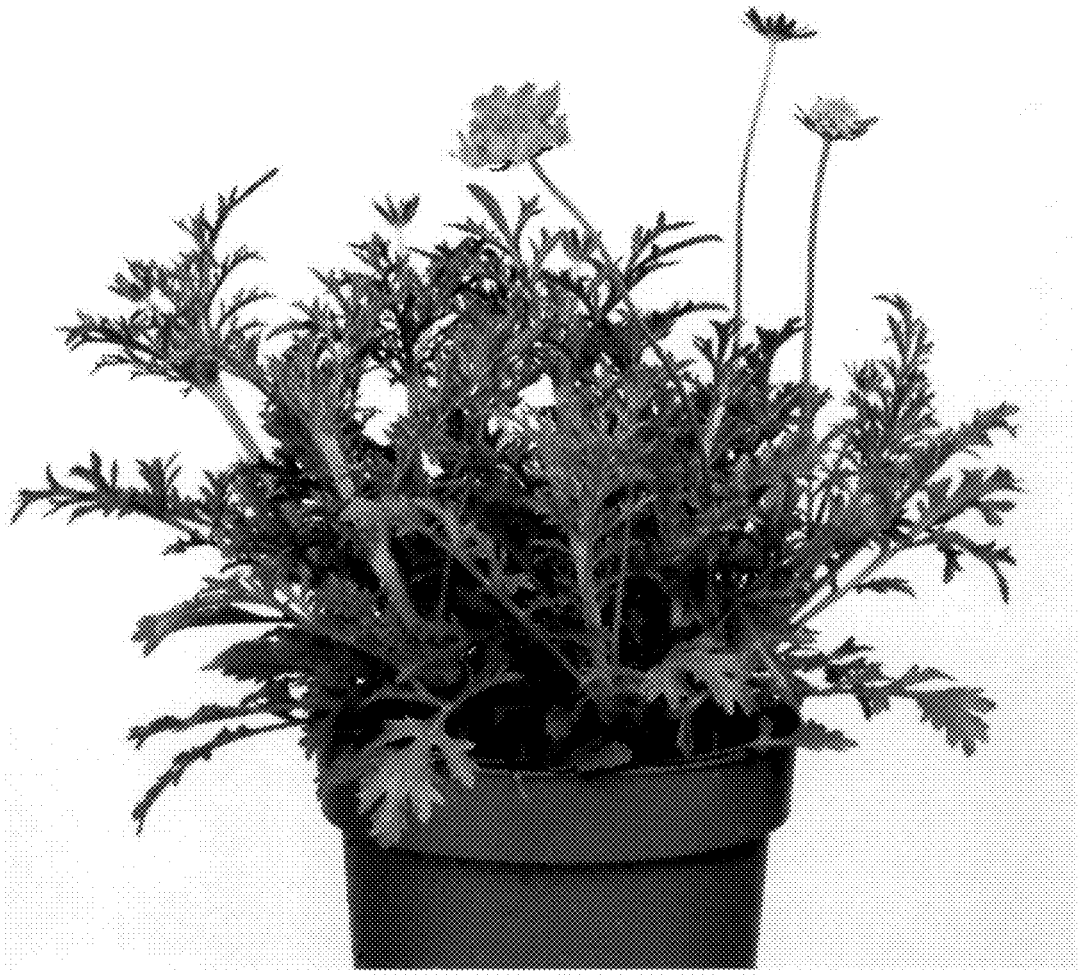
Figure 2:
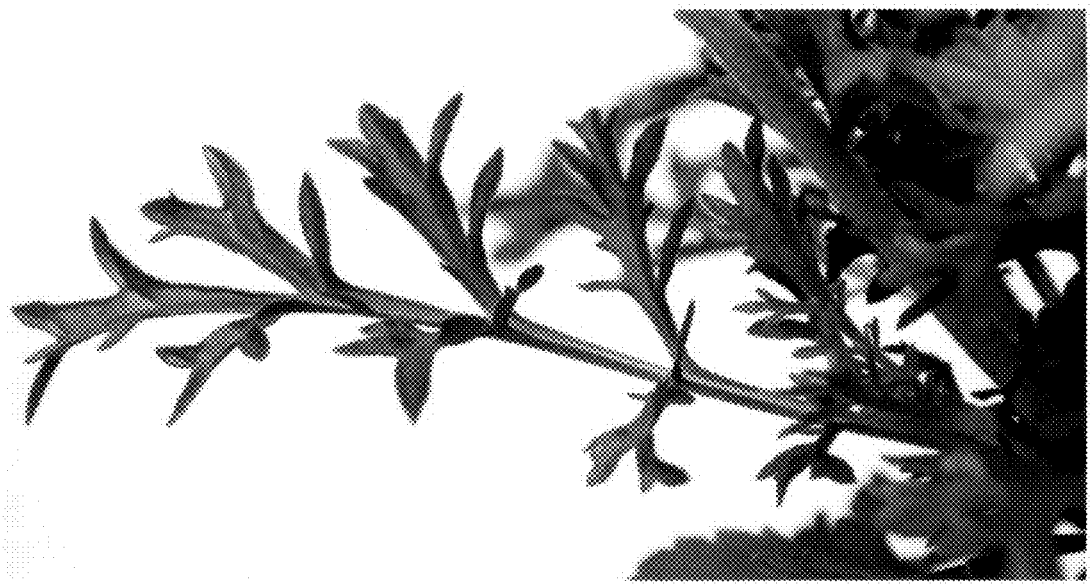

The photograph in FIG. 2 provides a close-up view of the foliage of 'Lier 01'.

Figure 3:
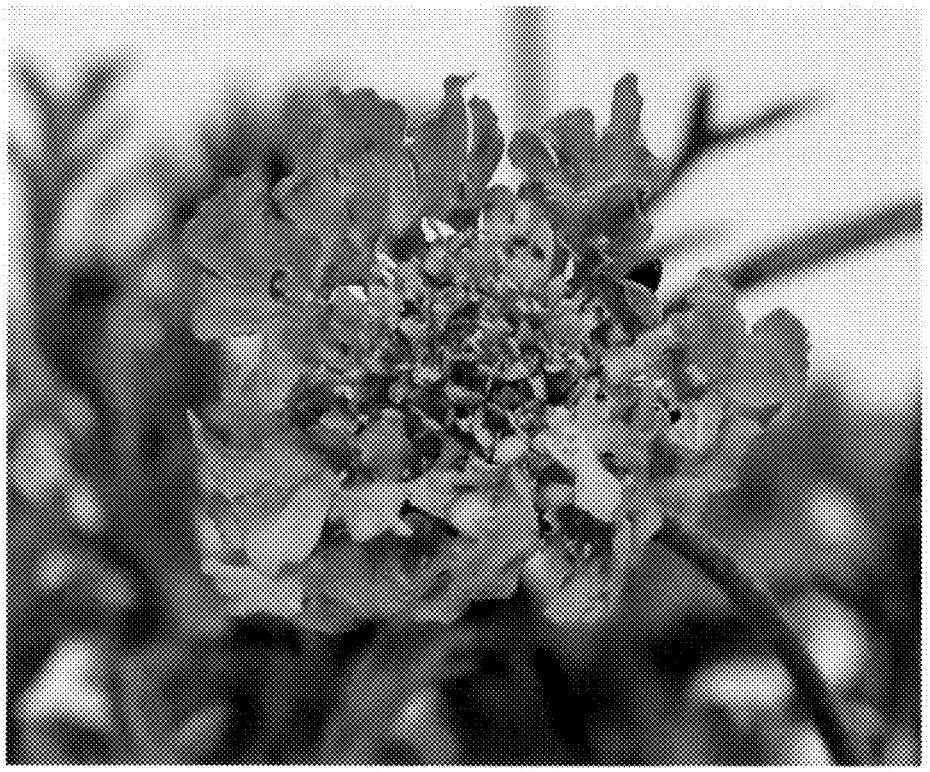

The photograph in FIG. 3 provides a close-up view of an inflorescence of 'Lier 01'.

The colors in the photographs may differ slightly from the color values cited in the detailed botanical description, which accurately describes the colors of the new *Scabiosa*.

DETAILED BOTANICAL DESCRIPTION

The following is a detailed description of 6-month-old plants of the new cultivar as grown outdoors in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—From June until first frost in The Netherlands.

*Plant habit*.—Herbaceous perennial, upright with extended flowering stems.

*Height and spread*.—Average of 18.8 cm in height (top of foliar plane), 25.3 cm in height (top of floral plane), and 35.8 cm in width as grown in a container, reaches an average of 40 cm in height and 60 cm in width in the landscape.

*Hardiness*.—At least in U.S.D.A Zones 4 to 6.

*Disease and pests*.—No susceptibility or resistance to diseases or pests has been observed.

*Root description*.—Fine and fibrous.

*Propagation*.—Stem cuttings.

*Root development*.—A rooted cuttings will fully develop as a finished plant in 15 weeks.

*Growth rate*.—Moderate.

Branch description:

*Branch shape*.—Rounded.

*Branch color*.—Young and mature 145A and 145B, internodes 145B and occasionally slightly tinged 176B.

Branch size.—9.7 cm in length, 5 mm in diameter.

*Internode length*.—Average of 4.1 cm.

*Branch surface*.—Slightly glossy, densely covered with short soft hairs that are 0.75 mm in length, N155A in color.

*Branch strength*.—Strong.

*Branching habit*.—Main stems grow from the base with lateral stems, main branches; 8, lateral branches; 2 per main branch.

Foliage description:

*Leaf division*.—Single.

*Leaf shape*.—Basal and lower stem leaves; runcinate, upper stem leaves; broadly ovate to broadly obovate.

*Leaf base*.—All leaves attenuate.

*Leaf apex*.—Basal and lower stem leaves; abruptly acute to acute, upper stem leaves; acute.

*Leaf margin*.—Basal and lower stem leaves; pinnatifid to pinnatisect, slightly to moderately undulate, lobes divergent with acute tips, upper stem leaves; pinnatisect, slightly to moderately undulate, lobes divergent, acute tips.

*Leaf venation*.—Pinnate, color; upper surface 145A, lower surface 144A.

*Leaf attachment*.—Petiolate.

*Leaf arrangement*.—Opposite.

*Leaf surface*.—All leaves; both surfaces slightly glossy, soft to the touch, margins densely covered with short soft hairs; 0.5 mm to 1 mm in length, N155A in color.

*Leaf color*.—All leaves; young upper surface 143B, young lower surface 144A, mature upper surface 137A, mature lower surface 146A.

*Leaf size*.—Basal and lower stem leaves; 7.6 cm in length, 3.2 cm in width, upper stem leaves; 11.6 cm in length, 5.8 cm in width.

*Leaf number*.—Average of 6 per branch.

*Leaf fragrance*.—None.

*Internode length*.—4.1 cm.

*Petiole*.—Flattened, basal and lower stem leaves; 4.1 cm in length, 4 mm in diameter, upper stem leaves; 1.6 cm in length, 2 mm in diameter, color; upper surface 145C, lower surface 145A and 145B.

Flower description:

*Inflorescence type*.—Terminal capitulum.

*Lastingness of inflorescence*.—Average of one week, self-cleaning.

*Inflorescence size*.—Average of 1.9 cm in height and 4.4 cm in width.

*Inflorescence fragrance*.—None.

*Inflorescence number*.—An average of 1 per stem.

*Flower quantity*.—An average of 100 per plant.

*Flower aspect*.—Outward to upright.

*Flower buds*.—Average of 6 mm in length, 3 mm in diameter, obovate in shape, color; 145C, tip is a blend of 70B and 186B.

*Corolla*.—Funnelform, marginal flowers; lower 50% fused into tube, 1.1 cm in height, 1.1 cm in diameter, 2.3 cm in depth, petals; 5, rotate, 1 whorl, 2 identical upper petals, 2 identical lateral petals, 1 lower petal, matte surface, smooth and glabrous, base is densely covered with very short pubescent hairs 0.2 mm in length, NN155D in color, upper and lateral petals obovate in shape, lower petal spathulate, 3-lobed, obtuse tips, base fused, entire margins, low to medium undulate, both surfaces smooth and glabrous, non-rugose, matte, lower surface moderately covered with very short pubescence, 0.2 mm in length, NN155D in color, size; upper 2 petals average of 2 mm in length, 3 mm in width, lateral petals 3 mm in length, 7 mm in width, lower petals 1.2 cm in length, 1.1 cm in width, color: when opening upper surface; N87C, when opening lower surface; 85A, central blotch N77B, when fully open upper surface; 84A, when fully open lower surface; 84A, central blotch N77B, central flowers; lower 70% fused into the tube, 3 mm in height, 4 mm in diameter, 1.1 cm in depth, petals; 5, rotate, 1 whorl, 2 identical upper petals, 2 identical lateral petals, 1 lower petal, matte surface, smooth and glabrous, base is densely covered with very short pubescent hairs 0.2 mm in length, NN155D in color, upper and lateral petals ovate, lower petals obovate, obtuse tips, base fused, entire margins, low to medium undulate, both surfaces smooth and glabrous, non-rugose, matte, lower surface moderately covered with very short pubescence, 0.2 mm in length, NN155D in color, size; upper 2 petals average of 2 mm in length, 1 mm in width, lateral petals 2.5 mm in length, 2 mm in width, lower petals 5 mm in length, 1.25 mm in width, color: when opening upper surface; 85A, lower petal lobe slightly darker; a blend of 84A and 84B, when opening lower surface; 85A and 85B, lateral lobe 84A, central blotch 197B, when fully open upper surface; N87C, lower petal lobe N87D, when opening lower surface; N87D, lateral lobe central blotch 197B.

*Sepals*.—5, upper surface smooth, slightly glossy, and glabrous, lower surface moderately covered with very short glandular hairs, average of 0.2 mm in length, matches surface color, linear in shape, entire margins, narrow acuminate apex, broadly cuneate base, 4 mm in length, 5 mm in width, color; young and mature upper and lower surfaces N79C to N94A, base 145D.

*Peduncles*.—21.6 cm in length and 2 mm in diameter, held in a vertical angle, strong, matte surface, 143B in color, densely covered with short soft hairs, an average of 0.4 mm in length, 157D in color.

*Calyx*.—Rotate, 4.5 mm in length, 4 mm in diameter in diameter.

*Pedicels*.—None, individual flowers sessile.

*Involucral bracts*.—14, arrangement is whorl around flower head, narrow oblong in shape, acute apex, broadly cuneate base, 1.1 cm in length, 2 mm in width, surfaces are smooth and glabrous, color; upper surface a blend of NN137B and 141A, lower surface NN137A.

Reproductive organs:

*Gynoecium*.—Pistil; 9 mm in length, stigma; 0.8 mm in diameter, cleft in shape, 84C in color, style; 8 mm in length, color 84A to 84B, proximal end NN155D, ovary; 145D in color.

*Androecium*.—Stamens; 2, filaments; 2 mm in length, NN155D in color, anthers; elliptic, dorsifixed, 1 mm in length, 0.5 mm in width, 162B in color, pollen; low in quantity, 163C in color.

*Fruit seeds*.—None observed to date.

It is claimed:

1. A new and distinct cultivar of *Scabiosa* plant named 'Lier 01' as herein illustrated and described.

* * * * *